(12) United States Patent
Linebarger

(10) Patent No.: US 12,201,389 B2
(45) Date of Patent: Jan. 21, 2025

(54) SYSTEMS AND METHODS FOR NETWORK BASED ELECTROSURGICAL DEVICE ACTIVATION

(71) Applicant: Covidien LP, Mansfield, MA (US)

(72) Inventor: John W. Linebarger, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 816 days.

(21) Appl. No.: 16/715,366

(22) Filed: Dec. 16, 2019

(65) Prior Publication Data

US 2020/0197116 A1 Jun. 25, 2020

Related U.S. Application Data

(60) Provisional application No. 62/782,798, filed on Dec. 20, 2018.

(51) Int. Cl.
| | | |
|---|---|---|
| *A61B 18/14* | (2006.01) | |
| *A61B 18/12* | (2006.01) | |
| *A61B 34/35* | (2016.01) | |
| *A61B 17/00* | (2006.01) | |
| *A61B 18/00* | (2006.01) | |
| *A61B 18/16* | (2006.01) | |
| *A61B 18/18* | (2006.01) | |
| *A61B 34/00* | (2016.01) | |

(52) U.S. Cl.
CPC .......... *A61B 34/35* (2016.02); *A61B 18/1206* (2013.01); *A61B 18/14* (2013.01); *A61B 2017/00199* (2013.01); *A61B 2017/00221* (2013.01); *A61B 17/00234* (2013.01); *A61B 2018/00589* (2013.01); *A61B 2018/00642* (2013.01); *A61B 2018/00678* (2013.01); *A61B 2018/00708* (2013.01); *A61B 2018/00875* (2013.01); *A61B 2018/00886* (2013.01); *A61B 2018/1253* (2013.01); *A61B 2018/126* (2013.01); *A61B 2018/1266* (2013.01); *A61B 18/1445* (2013.01); *A61B 18/16* (2013.01); *A61B 2018/1823* (2013.01); *A61B 34/25* (2016.02); *A61B 2034/742* (2016.02)

(58) Field of Classification Search
CPC ..... A61B 34/35; A61B 34/25; A61B 18/1206; A61B 18/14; A61B 2017/00221; A61B 2018/00678; A61B 2018/00708; A61B 2018/00886
See application file for complete search history.

(56) References Cited

U.S. PATENT DOCUMENTS 8,828,023 B2 9/2014 Neff et al.
2005/0251228 A1* 11/2005 Hamel .................. A61B 90/70
607/60
(Continued)

*Primary Examiner* — Sean W Collins

(57) ABSTRACT

A method for remote control of an electrosurgical device over a network is provided. The method including transmitting an activation request from a remote device to an electrosurgical device over a network, activating the electrosurgical device to output electrosurgical energy in response to receiving the activation request, starting a timer in response to receiving the activation request, and deactivating the electrosurgical device in response to at least one of the timer exceeding a predetermined time value or receiving a deactivation request from the remote device.

20 Claims, 7 Drawing Sheets

(56) References Cited

U.S. PATENT DOCUMENTS

| | | | |
|---|---|---|---|
| 2007/0066969 A1* | 3/2007 | McGreevy | A61B 18/1442 606/51 |
| 2012/0101413 A1* | 4/2012 | Beetel | A61B 18/1492 601/3 |
| 2013/0041368 A1* | 2/2013 | Cunningham | A61B 18/14 606/34 |
| 2015/0297282 A1* | 10/2015 | Cadouri | A61B 50/13 606/34 |
| 2019/0269457 A1* | 9/2019 | Schofield | A61B 18/1482 |
| 2021/0220064 A1* | 7/2021 | Kottenstette | A61B 34/25 |

* cited by examiner

SYSTEMS AND METHODS FOR NETWORK BASED ELECTROSURGICAL DEVICE ACTIVATION

BACKGROUND

Robotic surgical systems have been used in minimally invasive medical procedures. Some robotic surgical systems include a surgical robotic console supporting a surgical robotic arm and a surgical instrument, having at least one end effector (e.g., forceps, or a grasping tool), mounted to the robotic arm. The robotic arm provides mechanical power to the surgical instrument for its operation and movement. Each robotic arm may include an instrument drive unit that is operatively connected to the surgical instrument. Additionally, robotic surgical systems include surgical control consoles including a base, a visual assembly and controls to manipulate the surgical robotic arms of the surgical robotic console, that provide mechanical power to the surgical instrument for its operation and movement.

Some of the robotic surgical systems are used with various peripheral devices. However, in instances where such devices require instantaneous or near instantaneous activation there may be delays in transmitting commands to the peripheral devices due to latency inherent in some communication protocols. Accordingly there is a need for an improved communication protocol for interconnecting peripheral devices with robotic surgical systems.

SUMMARY

The present disclosure relates to systems and methods for method remote control of an electrosurgical device over a network.

In accordance with aspects of the present disclosure, a method for remote control of an electrosurgical device over a network is provided. The method including transmitting an activation request from a remote device to an electrosurgical generator over a network, activating the electrosurgical device to output electrosurgical energy in response to receiving the activation request, starting a timer in response to receiving the activation request, and deactivating the electrosurgical device in response to at least one of the timer exceeding a predetermined time value or receiving a deactivation request from the remote device. In an aspect of the present disclosure, the method further includes maintaining the output of electrosurgical energy with delays of the network being within the predetermined amount.

In an aspect of the present disclosure, the network is at least one of a wireless network or a wired network.

In another aspect of the present disclosure, if it is determined that the predetermined time value has not been exceeded, communicating a status, from the electrosurgical device to continue activating the electrosurgical generator to output electrosurgical energy.

In a further aspect of the present disclosure, the electrosurgical device is a generator.

In an aspect of the present disclosure, the electrosurgical device is an electrosurgical instrument.

In a further aspect of the present disclosure, the method further includes transmitting an operating status to the remote device over the network.

In yet a further aspect of the present disclosure, the operating status is transmitted continuously while the electrosurgical device is activated.

In another aspect of the present disclosure, the method further includes displaying the operating status on a remote surgical console display.

In accordance with aspects of the present disclosure, a method for remote control of an electrosurgical device over a network is provided. The method includes: receiving an activation request from a remote device to an electrosurgical device over a network, activating an electrosurgical device to output electrosurgical energy in response to receiving the activation request, starting a timer in response to receiving the activation request, and deactivating the electrosurgical device in response to at least one of the timer exceeding a predetermined time value or receiving a deactivation request from the remote device.

In an aspect of the present disclosure, if it is determined that the predetermined time value has not been exceeded, transmitting information regarding the operational status of the electrosurgical device over the network to the remote device and continuing to output electrosurgical energy.

In an aspect of the present disclosure, the method includes transmitting an operating status to the remote device over the network.

In another aspect of the present disclosure, the network is a wireless network.

In a further aspect of the present disclosure, the operating status is transmitted continuously while the electrosurgical device is activated.

In yet a further aspect of the present disclosure, the network is a wireless network.

In a further aspect of the present disclosure, the network is a wired network.

In another aspect of the present disclosure, the electrosurgical device is a generator.

In yet a further aspect of the present disclosure, the electrosurgical device is an electrosurgical instrument.

In accordance with aspects of the present disclosure, a system for remote control of an electrosurgical generator over a network is provided. The system includes: a first processor, and a first memory storing instructions. The instructions, when executed by the processor, cause the remote device to transmit an activation request to an electrosurgical device over a network, and the electrosurgical device configured for outputting electrosurgical energy in response to receiving the activation request, including: a second processor, and a second memory storing instructions. The instructions, when executed by the processor, cause the electrosurgical device to: activate electrosurgical energy in response to receiving the activation request, start a timer in response to receiving the activation request, and deactivate the electrosurgical device in response to at least one of the timer exceeding a predetermined time value or receiving a deactivation request from the remote device.

In an aspect of the present disclosure, the instructions, when executed by the second processor, further causes the electrosurgical device to transmit an operating status to the remote device over the network.

In another aspect of the present disclosure, the operating status is transmitted continuously while the device is activated. In a further aspect of the present disclosure, the remote device includes a display configured to display the operating status.

In a further aspect of the present disclosure, the network is at least one of a wireless network or a wired network.

In yet another aspect of the present disclosure, the electrosurgical device is at least one of an electrosurgical generator or an electrosurgical instrument.

Further details and aspects of exemplary embodiments of the present disclosure are described in more detail below with reference to the appended figures.

BRIEF DESCRIPTION OF DRAWINGS

Various aspects and features of the present disclosure are described herein below with reference to the drawings, wherein.

DETAILED DESCRIPTION

As used herein, the term "clinician" refers to a doctor, nurse, or other care provider and may include support personal. As used herein, the term "distal" refers to that portion of the mobile surgical control console, the robotic surgical system, or components thereof, that is farther from a clinician, while the term "proximal" refers to that portion of the mobile surgical control console, the robotic surgical system, or components thereof, that is closer to the clinician. Additionally, as used herein, the terms superior, inferior, anterior, and interior are used to describe portion of the mobile surgical control console, robotic surgical system, or components thereof, with the general understanding of the terms. In the following description, well-known functions or constructions are not described in detail to avoid obscuring the present disclosure in unnecessary detail. The term "network," whether plural or singular, as used herein, will be representative of a data network, including, but not limited to, the Internet, Intranets, wide area networks, and/or local area networks, and without limitation as to the full scope of the definition of data network as encompassed by the present invention.

As will be described in detailed below, provided is systems and methods for remote control of an electrosurgical device over a network. As will be disclosed in greater detailed below, the system for remote control of an electrosurgical device over a network includes an electrosurgical device configured for outputting electrosurgical energy and a remote activation device.

Figure 1:
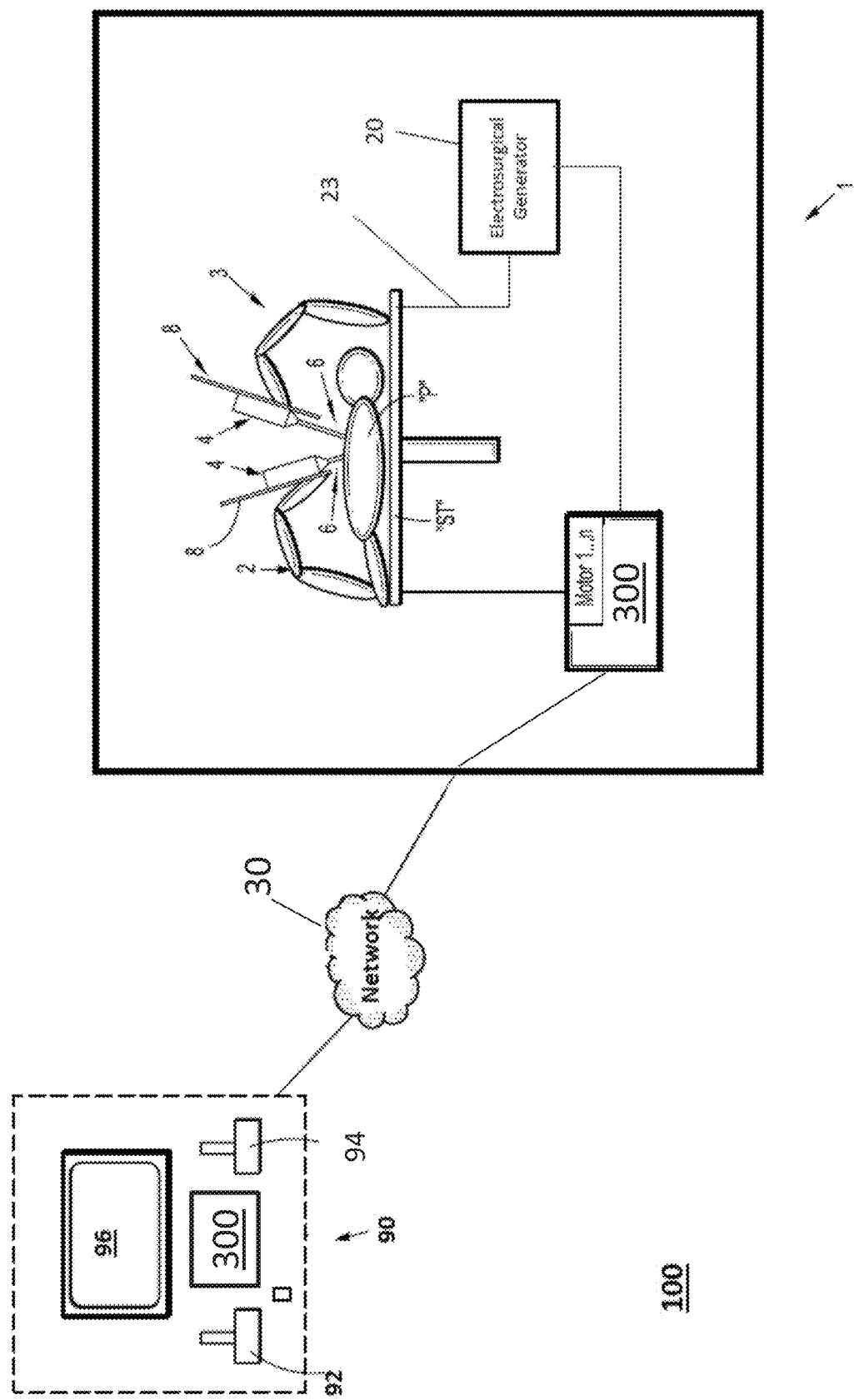
FIG. 1 is a schematic view of a robotic surgical system in accordance with the present disclosure.

Referring initially to FIG. 1, a surgical system, such as, for example, a robotic surgical system 1, generally includes one or more surgical robotic arms 2, 3, and an operating console, such as, for example, a remote activation device 90 coupled to computing device 300. In various embodiments, the remote activation device may include a mobile surgical control console. The robotic surgical system 1 is configured for use on a patient "P" positioned (e.g., lying) on a surgical table "ST" to be treated in a minimally invasive manner using the electromechanical surgical instrument 6. Any of the surgical robotic arms 2, 3 may have a robotic surgical assembly 4 and an electromechanical surgical instrument 6 coupled thereto. In some embodiments, the robotic surgical assembly 4 may be removably attached to a side rail 8 of one of the surgical robotic arms 2, 3. In certain embodiments, the robotic surgical assembly 4 may be fixedly attached to the side rail 8 of one of the surgical robotic arms 2, 3. The electromechanical surgical instrument 6, for example may include monopolar or bipolar electrosurgical devices, such as bipolar forceps.

Remote activation device 90, includes a display device, such as, for example, a monitor 96 set up to display three-dimensional images; and manual input devices 92, 94, which a clinician (not shown) uses to remotely control the surgical robotic arms 2, 3. Each of the surgical robotic arms 2, 3 may be composed of any number of members, which may be connected through joints. The surgical robotic arms 2, 3 may be driven by electric drives (not shown) that are connected to computing device 300. The computing device 300 (e.g., a computer or other control device) is set up to activate the drives, for example, by means of a computer program, in such a way that the surgical robotic arms 2, 3, the attached robotic surgical assembly 4, and thus the electromechanical surgical instrument 6 (including the electromechanical end effector, not shown) execute a desired movement according to a movement commands input through the manual input devices 92, 94. The computing device 300 may also be set up in such a way that it regulates the movement of the surgical robotic arms 2, 3, and/or of the drives automatically, e.g., according to predetermined movement algorithms.

The system 1 also includes an electrosurgical generator 20 and a cable 23 connecting the electrosurgical generator 20 and the electromechanical surgical instrument 6. The electrosurgical generator 20 can be any electrosurgical generator configured to output electrosurgical energy, which may be radio frequency electrical energy, microwave energy, direct current energy for providing resistive heating, and the like. In various embodiments, the cable 23 and the electromechanical surgical instrument 6 may be separable. In various embodiments, the cable 23 may be attached to the electromechanical surgical instrument 6 and may be inseparable from the electromechanical surgical instrument 6. The electrosurgical generator 20 includes a port 21 that receives the cable 23 (of FIG. 2). In various embodiments, the electromechanical surgical instrument 6 is a bipolar instrument and the port 21 of the electrosurgical generator 20 is a bipolar instrument port. As persons skilled in the art will recognize, a bipolar instrument receives electrical energy from a generator, applies a portion of the energy to treat tissue through an active electrode, and returns a portion of the energy back to the generator through a return electrode. In various embodiments, the electrosurgical instrument 10 can be another type of electrosurgical instrument, such as a monopolar instrument with a return pad electrode, and the electrosurgical generator 20 can include one or more corresponding ports 21, such as monopolar ports.

The remote activation device 90 may communicate with the robotic surgical system 1 over a network 30. The remote activation device 90 may be configured to connect to a wireless network. The remote activation device 90 may further transmit and/or receive data via a wireless interface via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

For a detailed discussion of the construction and operation of a robotic surgical system, reference may be made to U.S. Pat. No. 8,828,023, filed on Nov. 3, 2011, entitled "Medical Workstation," the entire contents of which are incorporated by reference herein.

Figure 2:
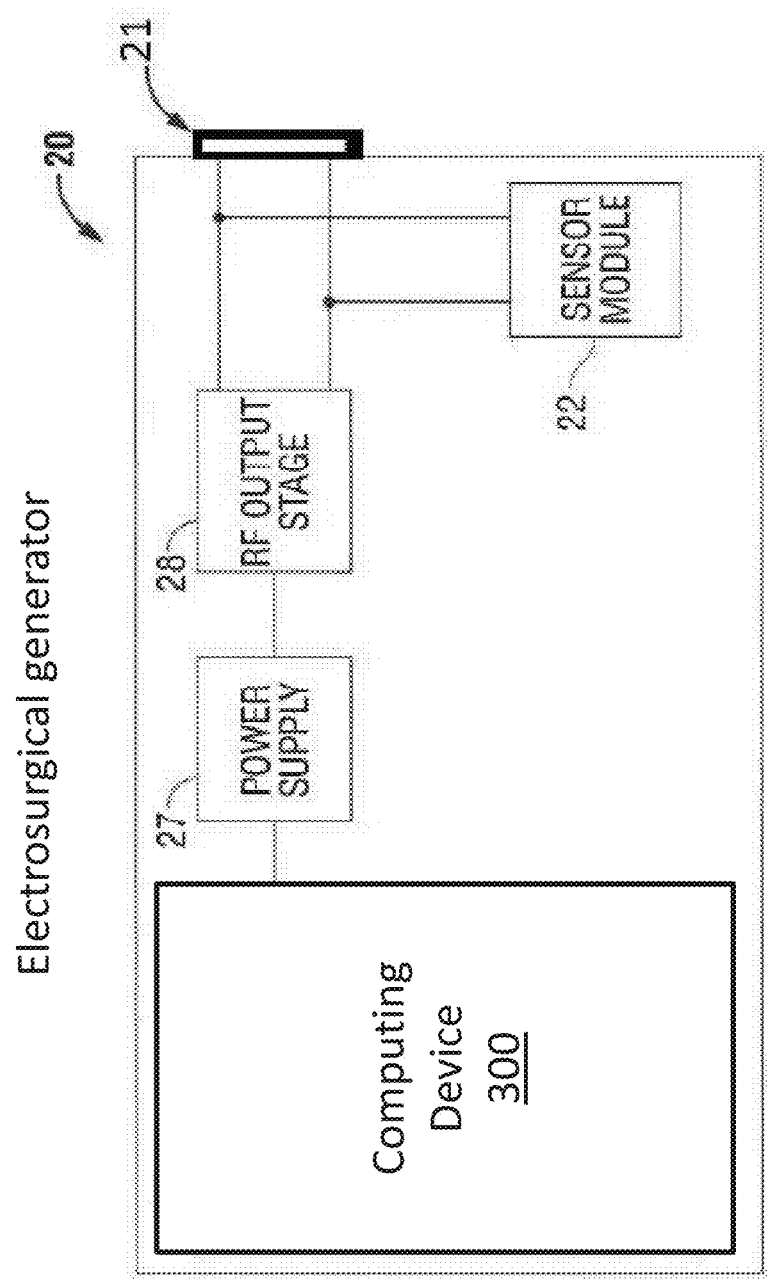
FIG. 2 is a block diagram of an electrosurgical generator of the robotic surgical system of FIG. 1, in accordance with the present disclosure.

With reference to FIG. 2, the electrosurgical generator 20 may include a user interface (not shown) that enables a user to set the electrosurgical generator 20 to provide electrical energy for different types of procedures. In various embodiments, the electrosurgical generator 20 may be set by a remote device to provide energy for different types of procedures. In various embodiments, the electrosurgical generator 20 can provide electrical energy for vessel coagulation, tissue dissection, or other types of electrosurgical procedures. Persons skilled in the art will understand the electrosurgical parameters generally suitable for such procedures. In various embodiments, the remote user interface (not shown) can include an energy setting that permits a user to specify an electrical energy for the electrosurgical generator 20 to provide to the electromechanical surgical instrument 6. The generator 20 includes a computing device 300, a DC power supply 27, an RF output stage 28, and a sensor module 22. The DC power supply 27 is connected to a conventional AC source (e.g., electrical wall outlet) and provides high voltage DC power to an RF output stage 28, which then converts high voltage DC power into RF energy and delivers the RF energy to a surgical device. The sensor module 22 senses that determines and continually monitors whether a tissue reacts to an electrode by sensing and recording a change in impedance over time.

Figure 3:
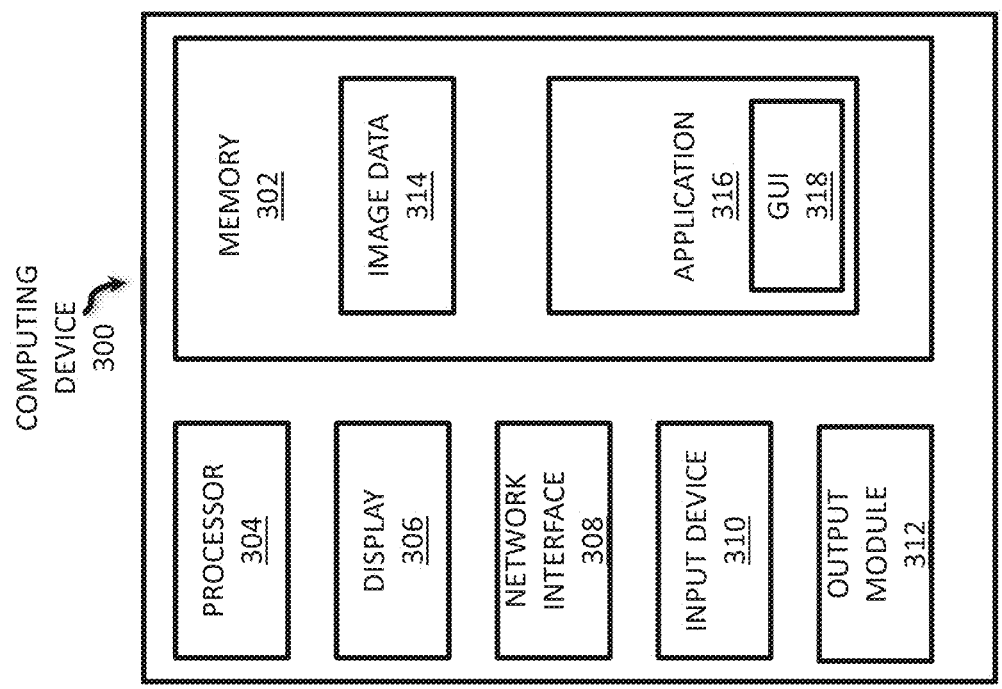
FIG. 3 is a block diagram of a computing device of the robotic surgical system of FIG. 1, in accordance with the present disclosure.

Referring now to FIG. 3, illustrated is a simplified block diagram of computing device 300. The computing device 300 may include a memory 302, a processor 304, a display 306, a network interface 308, an input device 310, and/or an output module 312. The memory 302 may store the application 316 and/or image data 314. The application 316 may, when executed by the processor 304, cause the display 306 to present a graphical user interface (GUI) 318 based on GUI instructions.

The memory 302 may include any non-transitory computer-readable storage media for storing data and/or software that is executable by the processor 304 and which controls the operation of the computing device 300. In an embodiment, the memory 302 may include one or more solid-state storage devices such as flash memory chips. Alternatively or in addition to the one or more solid-state storage devices, the memory 302 may include one or more mass storage devices connected to the processor 304 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 304. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 300.

The network interface 308 may be configured to connect to a network 30 (of FIG. 1.) such as a local area network (LAN) consisting of a wired network and/or a wireless network, a wide area network (WAN), a wireless mobile network, a Bluetooth network, and/or the internet. The input device 310 may be any device by means of which a user may interact with the computing device 300, such as, for example, a mouse, keyboard, foot pedal, touch screen, and/or voice interface. The output module 312 may include any connectivity port or bus, such as, for example, parallel ports, serial ports, universal serial busses (USB), or any other similar connectivity port known to those skilled in the art.

With reference to FIGS. 4-7, the flow diagrams include various blocks described in an ordered sequence. However, those skilled in the art will appreciate that one or more blocks of the flow diagram may be performed in a different order, repeated, and/or omitted without departing from the scope of the present disclosure. Further, the below description of the flow diagram refers to various actions or tasks performed by one or more computing devices 300, but those skilled in the art will appreciate that in some instances, the computing devices 300 perform the actions or tasks via one or more software applications, such as the application which could be firmware, executing on the computing devices 300.

Figure 4:
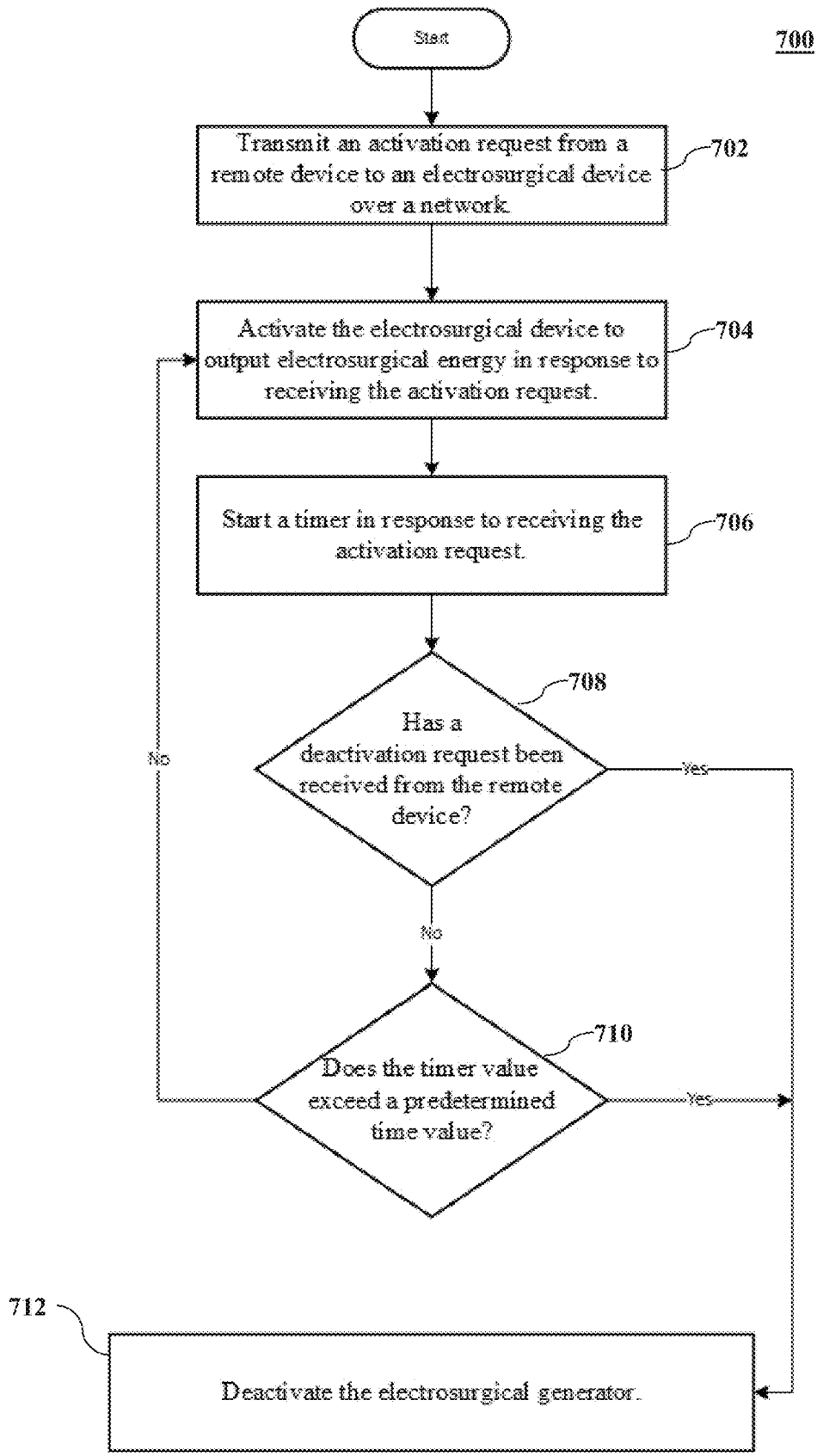
FIG. 4 is a flow diagram illustrative of a method for remote control of the electrosurgical generator of FIG. 2 over a network in accordance with the present disclosure

With reference to FIG. 4, is a flow diagram 700 illustrative of a method for remote control of an electrosurgical device over a network 30 in accordance with the present disclosure. Initially at block 702, the remote activation device 90 transmits an activation request to the electrosurgical generator 20 over a network 30. The remote activation device 90 may be any user input device, such as a button, a switch, a graphical user interface, incorporated into or otherwise a part of the remote activation device 90. The electrosurgical device may be the electrosurgical generator 20 and/or an electrosurgical instrument, e.g., electromechanical surgical instrument 6. The request may include a signal that may be used to activate the electrosurgical device. In various embodiments, manual input devices 92, 94, (of FIG. 1) which a clinician uses to remotely control the electrosurgical device may include latching or non-latching switches to activate the electrosurgical energy from the electrosurgical device.

At block 704 the electrosurgical device is activated to output electrosurgical energy in response to receiving the activation request. In various embodiments, the electrosurgical device may transmit an operational status over the network 30 to the remote activation device 90. The electrosurgical device may include a continuous activation of electrosurgical energy. In various embodiments, the electrosurgical device may include two operating modes: in a first mode the electrosurgical device outputs electrosurgical energy, and a second mode during which the electrosurgical device is deactivated and is not outputting the electrosurgical energy. Thus, at block 704, the electrosurgical device is operating in the first mode. In various embodiments, the remote activation device 90 detects information regarding an operational status of the electrosurgical generator 20 over the network 30. In embodiments, the electrosurgical generator 20 may operate in multiple modes, each of which may be associated with different functionalities of the generator, such as stand-by mode, device authentication, mode, and the like.

At block 706, the electrosurgical device starts a timer. In various embodiments, the timer is started from zero each time an activation request is received. In various embodiments, the electrosurgical device may include an electrosurgical generator 20.

At block 708, the electrosurgical device determines if a deactivation request has been received from the remote activation device 90. If the deactivation request has been received by the electrosurgical device from the remote activation device 90, ("Yes" at block 708) then the electrosurgical device enters a second mode and deactivates the electrosurgical energy (block 712). In various embodiments, the electrosurgical device may then communicate the operational status over the network 30 to the remote activation device 90.

If the deactivation request has not been received, ("No" at block 708) then block 710, the electrosurgical device determines if the timer reaches a predetermined value. At block 710, if the electrosurgical device determines the timer reaches the predetermined value, ("Yes" at block 710) then the electrosurgical device enters the second mode and deactivates the electrosurgical energy (block 712).

In various embodiments, information regarding the operational status of the electrosurgical device indicating that the electrosurgical energy has been deactivated is transmitted across the network 30 to the remote activation device 90 to detect any network 30 latency. For example, network interruptions or excessive network traffic may cause the deactivation request additional delay in being received by the remote activation device 90. In various embodiments, if the timer value did not exceed the predetermined value, for example 250 msec the remote activation device 90 returns to detecting information regarding an operational status of the electrosurgical generator 20 over the network 30.

Figure 5:
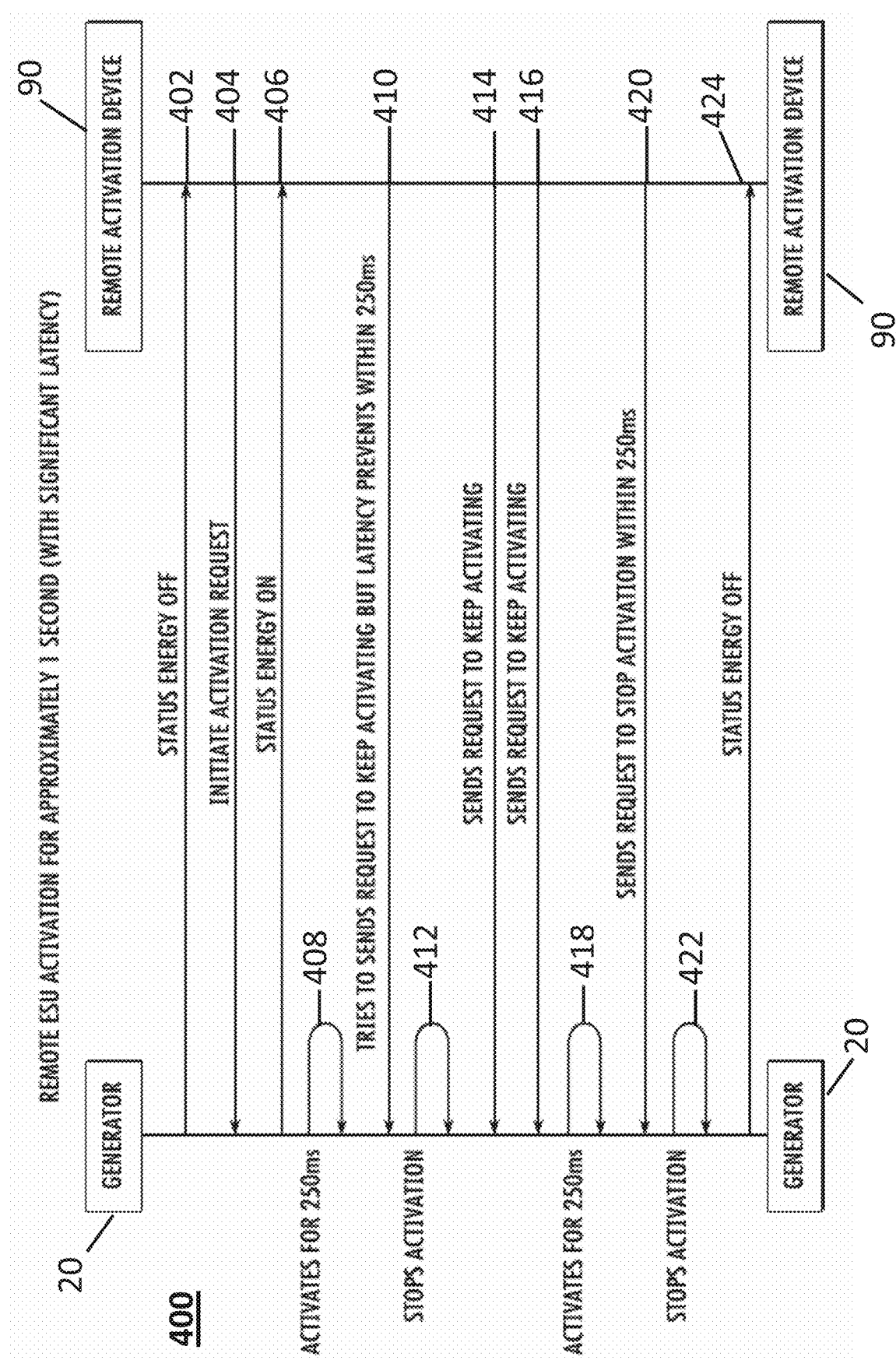
FIG. 5 is a flow diagram of communication signals between a remote electrosurgical generator and a remote activation device illustrating latency, in accordance with the present disclosure.

FIG. 5 illustrates operation of the electrosurgical generator 20 on the network 30 having significant latency, e.g., 1 sec or above. In particular, FIG. 5 shows a flow diagram of communication signals between the electrosurgical generator 20 and the remote activation device 90 with significant latency. Initially, at block 402, the electrosurgical generator 20 transmits a status to the remote activation device 90. In various embodiments, the button or switch may include a latching or non-latching switch or button.

At block 404, the remote activation device 90 transmits a request to the electrosurgical generator 20 to initiate activation of electrosurgical energy. At block 406, the electrosurgical generator 20 transmits to the remote activation device 90 a status that the electrosurgical energy is "On," the electrosurgical generator 20 is operating in the first mode, and begins a timer from zero. In this example, the timer is set for a predetermined latency period, which may be about 250 milliseconds (msec). However, the latency period could be any length of time that would be suitable in a system to denote a significant latency. The latency period may be adjustable during configuration of the robotic surgical system 1.

In embodiments, the robotic surgical system 1 may continuously measure latency of the network by continuously "pinging" each of the network components, and updating the latency period based on the measured latency to coincide with the actual network latency.

At block 408, the electrosurgical generator 20 activates the electrosurgical energy while the timer counts until the latency period of 250 msec expires. At block 410, the remote activation device 90 attempts to send a request to the electrosurgical generator 20 to keep activating the energy, however, 250 msec has already elapsed prior to this request being received by the electrosurgical generator 20. At block 412 the electrosurgical generator stops activation of the electrosurgical energy. At block 414, the remote activation device 90 attempts again to send a request to the electrosurgical generator 20 to keep activating the energy. At block 416, the remote activation device 90 attempts again to send a request to the electrosurgical generator 20 to keep activating the energy and the electrosurgical generator 20 receives the request.

At block 418, the electrosurgical generator 20 activates the electrosurgical energy in response to the request sent in block 416 by the remote activation device 90. Here, the timer restarts at zero when the electrosurgical generator 20 begins activation of energy. At block 420, the remote activation device 90 sends a request to stop activation within 250 msec. At block 422, in response to this request, the electrosurgical generator stops activation. At block 422, the electro surgical generator stops activation. Finally, at block 424, the electrosurgical generator 20 transmits a status of energy "Off" to the remote activation device 90, the electrosurgical generator 20 is in the second mode.

Figure 6:
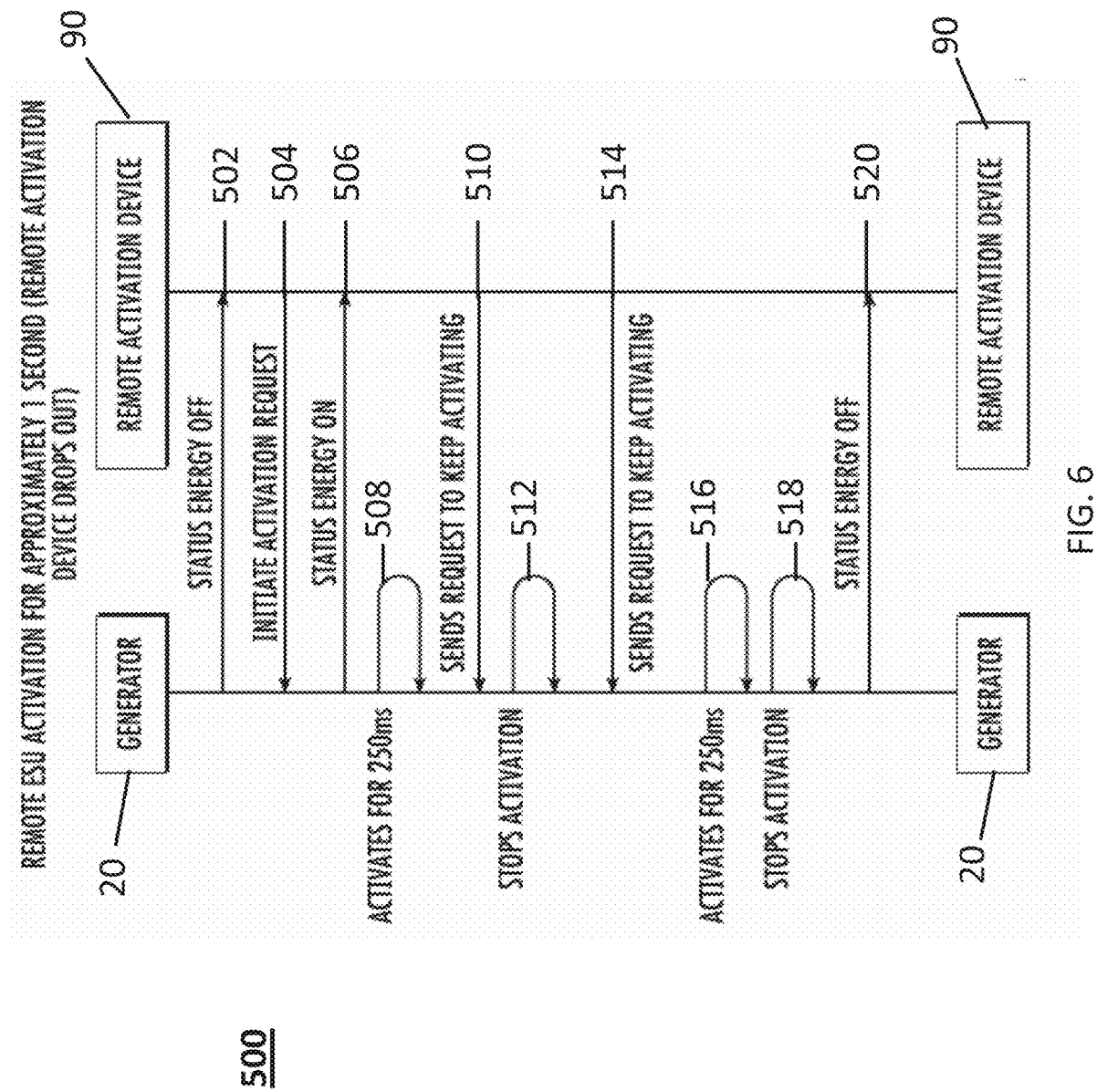
FIG. 6 is a flow diagram of a remote electrosurgical generator activation where the remote activation device drops out, in accordance with the present disclosure.

With reference to FIG. 6, a flow diagram of a remote electrosurgical generator 20 activation for approximately 1 sec where the remote activation device 90 drops out, where the remote activation device drops out, is presented in accordance with the present disclosure. Initially, at block 502, the electrosurgical generator 20 transmits a status to the remote activation device 90, which may include surgical control consoles. The status indicating that the electrosurgical generator's 20 output electrosurgical energy is "Off," the electrosurgical generator 20 is operating in the second mode. At block 504, the remote activation device 90 transmits a request to the electrosurgical generator 20 to initiate activation of electrosurgical energy. At block 506, the electrosurgical generator 20 transmits to the remote activation device 90 a status that the electrosurgical energy is "On," the electrosurgical generator 20 is in the first mode, and begins a timer from zero. In this example, the timer is set for a predetermined 250 msec. At block 508, the electrosurgical generator 20 activates electrosurgical energy. At block 510, the remote activation device 90 transmits a request to the electrosurgical generator 20 to keep activating, and it is received by the electrosurgical generator 20 before the timer reaches 250 msec. At block 512, the electrosurgical generator 20 stops activation of the electrosurgical energy, the electrosurgical generator 20 is in the second mode. This restarts the timer at zero.

At block 514, the remote activation device 90 transmits a request to the electrosurgical generator 20 to keep activating, and it is received by the electrosurgical generator 20. At block 516, the electrosurgical generator activates for another 250 msec. If the timer reaches 250 msec and no request to keep activating by the remote activation device 90 was received by the electrosurgical generator 20, the electrosurgical generator 20 stops activation of the electrosurgical energy (block 518), namely, the electrosurgical generator 20 is in the second mode. At block 520, the electrosurgical generator 20 transmits an electrosurgical energy "Off" status to the remote activation device 90.

Figure 7:
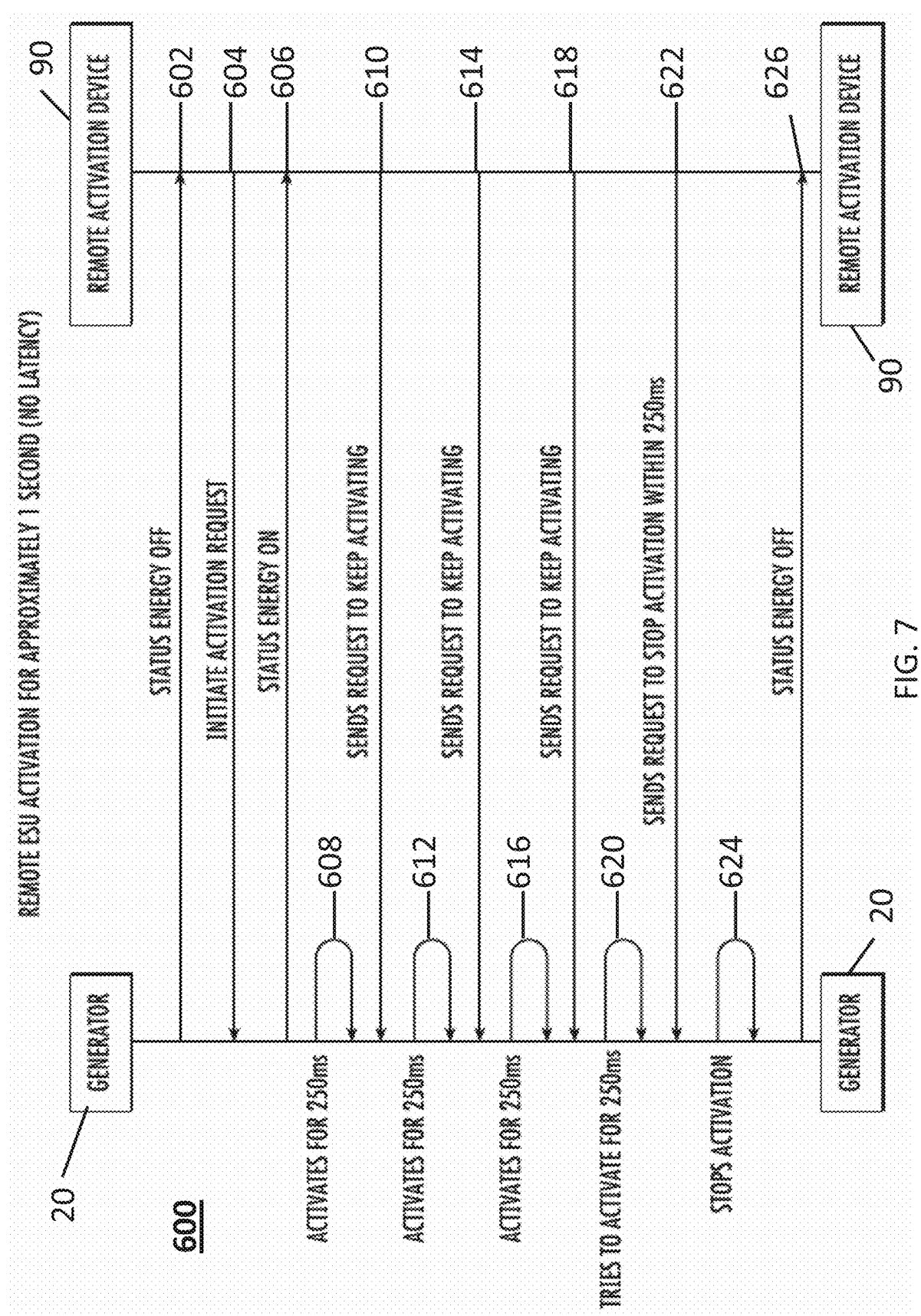
FIG. 7 is a flow diagram of a remote electrosurgical generator activation where the remote activation device drops out.

With reference to FIG. 7, a flow diagram 600 of a remote electrosurgical generator 20 activation for approximately 1 second, with no latency, is presented in accordance with the present disclosure. Initially, at block 602, the electrosurgical generator 20 transmits a status, over a network 30, to the remote activation device 90, which may include surgical control consoles. At block 604, the remote activation device 90 transmits a request to the electrosurgical generator 20 to initiate activation of electrosurgical energy. At block 606, the electrosurgical generator 20 transmits to the remote activation device 90 a status that the electrosurgical energy is "On," the electrosurgical generator 20 is in the first mode, and begins a timer from zero. In this example, the timer is set for a predetermined 250 msec. At block 608, the electrosurgical generator 20 activates electrosurgical energy for less than 250 msec. At block 610, the remote activation device 90 transmits a request to the electrosurgical generator 20 to keep activating, and it is received by the electrosurgical generator 20 before the timer reaches 250 msec. This restarts the timer at zero. At block 612, the electrosurgical generator 20 activates for another 250 msec.

At block 614, the remote activation device 90 transmits a request to the electrosurgical generator 20 to keep activating, and it is received by the electrosurgical generator 20 before the timer reaches 250 msec. This restarts the timer at zero. At block 616, the electrosurgical generator 20 activates for another 250 msec. At block 618, the remote activation device 90 transmits a request to the electrosurgical generator 20 to keep activating, and it is received by the electrosurgical generator 20 before the timer reaches 250 msec. This restarts the timer at zero. At block 620, the electrosurgical generator 20 activates for another 250 msec. At block 622, the remote activation device 90 transmits a request to the electrosurgical generator 20 to stop activation within 250 msec. The electrosurgical generator 20 stops outputting electrosurgical energy at block 624 in response to this request. At block 626 the electrosurgical generator 20 transmits an electrosurgical energy "Off" status to the remote activation device 90 namely, the electrosurgical generator 20 is in the second mode.

It will be understood that various modifications may be made to the embodiments of the presently disclosed mobile surgical consoles. The present disclosure may be used to control any medical device rather than just electrosurgical generators over a communication network where latency may be an issue. Therefore, the above description should not be construed as limiting, but merely as exemplification of embodiments. Those skilled in the art will envision other modifications within the scope and spirit of the present disclosure.

What is claimed is:

1. A method for remote control of an electrosurgical device over a network, the method comprising:
   receiving, by the electrosurgical device over the network, a first activation request from a remote device, with the electrosurgical device being operable in a first mode wherein the electrosurgical device outputs electrosurgical energy, and in a second mode wherein the electrosurgical device does not output electrosurgical energy;
   in response to the first activation request, starting a latency timer from zero;
   receiving, by the electrosurgical device over the network, a second activation request from the remote device;
   in response to the second activation request, comparing the latency timer with a predetermined latency value; and
   when the latency timer meets or exceeds the predetermined latency value, operating the electrosurgical device in the second mode.

2. The method according to claim 1, further comprising:
   in response to the first activation request, operating the electrosurgical device in the first mode.

3. The method according to claim 2, further comprising:
   in response to the second activation request, operating the electrosurgical device in the first mode when the latency timer does not exceed the predetermined latency value.

4. The method according to claim 1, further comprising:
   in response to at least one of the first activation request or the second activation request, operating in the first mode to continuously output electrosurgical energy for a predetermined time interval equal to the predetermined latency value.

5. The method according to claim 1, further comprising modifying the predetermined latency value during operation of the electrosurgical device.

6. The method according to claim 1, further comprising:
   measuring a latency of the network by pinging at least one network component over the network; and
   modifying the predetermined latency value based on the measured latency.

7. The method according to claim 1, further comprising:
   monitoring, by the electrosurgical device, the network for a deactivation request; and
   in response to receiving the deactivation request, operating the electrosurgical device in the second mode.

8. The method according to claim 1, further comprising transmitting, by the electrosurgical device, an operating status to the remote device over the network.

9. The method according to claim 8, wherein the operating status is transmitted continuously while the electrosurgical device is in the first mode.

10. A system for remote control of an electrosurgical device over a network, comprising:
    a remote device comprising a first processor and a first memory storing first instructions which, when executed by the first processor, cause the remote device to transmit a first activation request and a second activation request over the network; and
    an electrosurgical device operable in a first mode wherein the electrosurgical device outputs electrosurgical energy, and in a second mode wherein the electrosurgical device does not output electrosurgical energy, the electrosurgical device comprising:
    a second processor configured to receive the first activation request and the second activation request; and
    a second memory storing second instructions which, when executed by the second processor, cause the electrosurgical device to:
    start a latency timer from zero in response to the first activation request;
    compare the latency timer to a predetermined latency value in response to the second activation request; and
    when the latency timer meets or exceeds the predetermined latency value, operate in the second mode.

11. The system according to claim 10, wherein the second instructions further cause the electrosurgical device to operate in the first mode to continuously output electrosurgical energy for a predetermined time interval equal to the predetermined latency value.

12. The system according to claim 10, wherein the second instructions further cause the electrosurgical device to modify the predetermined latency value during operation of the electrosurgical device.

13. The system according to claim 10, wherein the second instructions, when executed by the second processor, further cause the electrosurgical device to transmit an operating status to the remote device over the network.

14. The system according to claim 13, wherein the operating status is transmitted continuously while the electrosurgical device is operated in the first mode.

15. The system according to claim 13, wherein the remote device includes a display configured to display the operating status.

16. The system according to claim 10, wherein the network comprises a wireless network.

17. The system according to claim 10, wherein the electrosurgical device comprises at least one of an electrosurgical generator or an electrosurgical instrument.

18. An electrosurgical device, comprising:
   a power supply and an output port operably coupled thereto, with the electrosurgical device operable in a first mode wherein the output port provides electrosurgical energy, and in a second mode wherein the output port does not provide electrosurgical energy; and
   a computing device operably coupled to the power supply and comprising a processor configured for signal communication over a network and receiving a first activation request and a second activation request, and also comprising a memory storing instructions for execution by the processor;
   wherein the computing device is configured to:
      operate the electrosurgical device in the first mode in response to the first activation request;
      start a latency timer from zero in response to the first activation request;
      compare the latency timer to a predetermined latency value in response to the second activation request; and
      when the latency timer meets or exceeds the predetermined latency value, operate the electrosurgical device in the second mode.

19. The electrosurgical device according to claim 18, wherein the computing device is further configured to operate the electrosurgical device in the first mode when the latency timer does not exceed the predetermined latency value.

20. The electrosurgical device according to claim 18, wherein the computing device is further configured to modify the predetermined latency value during operation of the electrosurgical device.

\* \* \* \* \*